United States Patent
Bulled et al.

(10) Patent No.: US 7,549,315 B2
(45) Date of Patent: Jun. 23, 2009

(54) PROTOCOL FOR CHARACTERIZING ROCK, METHOD FOR CHARACTERIZING ROCK HARDNESS AND METHODS FOR USE THEREWITH

(75) Inventors: David Bulled, Richmond Hill (CA); Khiratt Husain, North York (CA)

(73) Assignee: SGS Lakefield Research, Ltd., Toronto, Ontario (CA)

( * ) Notice: Subject to any disclaimer, the term of this patent is extended or adjusted under 35 U.S.C. 154(b) by 116 days.

(21) Appl. No.: 11/863,800

(22) Filed: Sep. 28, 2007

(65) Prior Publication Data

US 2009/0084168 A1   Apr. 2, 2009

(51) Int. Cl.
*G01L 5/00* (2006.01)
*G01N 3/08* (2006.01)

(52) U.S. Cl. .................. 73/11.01; 73/821
(58) Field of Classification Search ............ 73/11.01, 73/803, 818, 821, 825; 241/140, 207
See application file for complete search history.

(56) References Cited

U.S. PATENT DOCUMENTS

| | | | | |
|---|---|---|---|---|
| 3,638,870 A | * | 2/1972 | Ferris | 241/140 |
| 4,049,056 A | * | 9/1977 | Godfrey | 166/299 |
| 4,410,145 A | * | 10/1983 | Koch | 241/264 |
| 4,575,014 A | * | 3/1986 | Szalanski et al. | 340/853.5 |
| 4,588,137 A | * | 5/1986 | McConnell, Jr. | 241/156 |
| 4,875,628 A | * | 10/1989 | Knobloch et al. | 241/24.1 |
| 5,767,399 A | * | 6/1998 | Smith et al. | 73/152.11 |
| 5,769,340 A | * | 6/1998 | Jean | 241/207 |
| 6,513,424 B1 | * | 2/2003 | Iwasaki et al. | 100/40 |
| 2004/0035967 A1 | * | 2/2004 | Johnson et al. | 241/207 |

OTHER PUBLICATIONS

Stephen Morrell, "Rock Characterization for High Pressure Grinding Rolls Circuit Design", SAG Conference 2006. Department of Mining Engineering University of British Columbia, pp. IV-267-IV-278.
Morrell S., "Predicting the Specific Energy of Autogenous and Semi-autogenous Mills from Small Diameter Drill Core Samples", SAG Mill Comminution (SMC) Test, Minerals Engineering, vol. 17/3, pp. 447-451.
Napier-Munn, T.J., "Mineral Comminution—Their Operation and Optimisation", JK Drop-Weight Test, Chapter 4, JKMRC Monograph Series in Mining and Mineral Processing 2, p. 15.

* cited by examiner

*Primary Examiner*—Jewel Thompson
(74) *Attorney, Agent, or Firm*—Volpe and Koenig, P.C.

(57) ABSTRACT

A protocol for characterizing a rock is provided. The protocol includes a crushing operation, wherein a test column of the rock in granular form is subjected to a compressive force orientated parallel to the axis of the column. The protocol further includes a measurement operation, wherein the amount by which the axial length of the test column is reduced through the application of the force is measured. The protocol yet further includes a calculation operation, wherein a characteristic of the rock is calculated using the product of the force applied and the amount by which the length of the test column is reduced through the application of the force. A method for characterizing the hardness of a subject rock is also provided.

16 Claims, 3 Drawing Sheets

PROTOCOL FOR CHARACTERIZING ROCK, METHOD FOR CHARACTERIZING ROCK HARDNESS AND METHODS FOR USE THEREWITH

FIELD OF THE INVENTION

The invention relates to the field of rock crushing.

BACKGROUND OF THE INVENTION

Rock crushing is commonplace in industry. For example, in the mineral processing industry, ore samples are routinely crushed to liberation sizes in order to separate the valuable minerals from the waste rock. High pressure grinding rolls, termed HPGR, are commonly used for this purpose. It is often advantageous to know the specific energy required to crush a particular type of rock, as this can be of assistance in sizing electrical services and in equipment selection in plant design. Existing methods for calculating crushing energy generally require about 250 kilograms of rock sample and base the energy analysis on electrical energy consumed during a crushing operation. The large sample masses required renders these methods inconvenient.

SUMMARY OF THE INVENTION

The invention, according to one aspect, involves the characterization of rock hardness using a measurement of mechanical energy made in a crushing operation.

A protocol for characterizing a rock forms one aspect of the invention. The protocol comprises a crushing operation, a measurement operation and a calculation operation. In the crushing operation, a test column of said rock in granular form is subjected to a compressive force orientated parallel to the axis of said column. In the measurement operation, the amount by which the axial length of the test column is reduced through the application of the force is measured. In the calculation operation, the product of the force applied and the amount by which the length of the test column is reduced through the application of the force is calculated to characterize said rock.

In the crushing operation, the force can be increased over time; in the measurement operation, the distance by which the test column contracts as the force is increased can be dynamically measured; and in the calculation operation, the product of the force applied and the amount by which the length of the test column is reduced can be calculated as an integral.

In the crushing operation the force can be increased to a predetermined maximum and at least until visible breakage of said rock is apparent throughout the axial extent of the test column.

In the protocol: (i) a granular supply of the rock can be provided; (ii) taken from the granular supply can be a portion equal in mass to the test column; (iii) the portion can be formed into a precursor column; (iv) the precursor column can be subjected to a crushing operation to form a compressed column; (v) the fines can be removed from the compressed column; (vi) the portion can be replenished with an amount of the granular supply equal in mass to the fines removed; and (vii) steps (iii)-(v) can be repeated until the amount of the fines removed each time in step (v) has stabilized.

The final precursor column in the series can define the test column.

The granular supply can be obtained by crushing said rock to 100% passing through about 19000 micron mesh.

In step (v) the fines can be removed from the compressed column by screening out the particles smaller than about 3350 microns.

The amount of fines removed can be deemed to have stabilized when the amount of fines removed in a respective step (v) is within 3% by mass of the amount of fines removed in the previous step (v) and there is no increasing or decreasing trend in terms of the mass of the fines removed in the respective step (v), said previous step (v) and in the step (v) preceding said previous step (v).

In the crushing operation performed on each precursor column, the force can be increased over time to said predetermined maximum; the amount by which the axial length of each precursor column is reduced in the crushing operation performed thereon can be dynamically measured as the force is increased; and a product of the force applied to each precursor column and the amount by which the length of said each precursor column is reduced as the force is increased can be calculated as an integral.

In the calculation operation, the arithmetic average of the integrals calculated in respect of the test column and the two precursor columns preceding the test column can be used to characterize the rock.

A method for characterizing the hardness of a rock forms another aspect of the invention. The method comprises the steps of:

i. characterizing, using the protocol, the rock; and
ii. characterizing the extent of the breakage experienced by the test column in the crushing operation performed thereon; and
iii. characterizing the rock hardness as a function of the characteristic of the rock and of the extent of the breakage.

The hardness of the rock can be characterized using the formula $$HPI = \frac{E_m}{M \times (P_{80}^{-0.5} - F_{80}^{-0.5})}$$

where
HPI is the characterized rock hardness
$E_m$ is the characteristic of the rock
$F_{80}$ is the aperture size through which will pass 80% by mass of said equal amount by mass of the granular supply
$P_{80}$ is the aperture size through which will pass 80% by mass of the fines removed from the test column after the crushing operation is performed thereon
M is the mass of the amount of fines removed from the test column after the crushing operation was performed thereon A method for calculating the amount of energy required to crush a rock from a feed size to a product size forms another aspect of the invention. This method comprises the steps of:

i. characterizing the hardness of the rock according to the invention;
ii. calculating the amount of energy required to crush the rock using the formula $$E = HPI \times M \times (P_{80}^{-0.5} - F_{80}^{-0.5})$$

where
HPI is the characterized hardness of the rock
M is the mass of rock to be crushed
E is the energy required to crush the mass of rock $F_{80}$ is the feed size, defined as the aperture size through which will pass 80% by mass of the particles to be crushed $P_{80}$ is the product size, defined as the aperture size through which will pass 80% by mass of the particles after crushing Forming another aspect of the invention is a method for estimating the capacity of a crusher to crush a subject rock, said crusher having a known capacity for crushing a known rock. The method comprises the steps of:

i. characterizing according to the invention the hardness of the subject rock and of the known rock; and ii. calculating the product of the known capacity and the ratio of the hardnesses characterized in (i) to arrive at the capacity of the crusher for crushing the subject rock.

In the method, in each crushing operation, the force can be increased until the aggregate void volume of the respective compressed column is equivalent to the aggregate void volume of the output of the crusher.

An advantage associated with the protocol is that it permits relatively accurate calculations of:

the amount of energy required to crush a rock from a feed size to a product size; and the capacity of a crusher to crush a subject rock, said crusher having a known capacity for crushing a known rock, on the basis of relatively small sample sizes in comparison to known methods.

Other advantages, features and characteristics of the present invention will become more apparent upon consideration of the following detailed description and the appended claims with reference to the accompanying drawings, the latter being briefly described hereinbelow.

DESCRIPTION

An exemplary embodiment of the protocol of the present invention will now be described in detail.

To carry out the exemplary protocol, a column of rock needs to be provided. For the purpose of this description, "rock" should be understood as including, but not being limited to, mineral-bearing ores.

To prepare the column, about a 6 kg supply of the rock is crushed in a conventional mariner until a granular supply is formed wherein 100% will pass through a 19000 micron mesh. For the purpose of this disclosure and the accompanying claims, a "granular supply" should be understood as including, but not being limited to, a "particulate supply". About 2 kg of this material is placed into a cylindrical sample holder and slightly rammed such that the granular material assumes a columnar shape having a bulk density which approximates the average bulk density of the supply. This column is then subjected to a crushing operation in which it is rammed and thereby subjected to a compressive force orientated parallel to the column axis which is increased over time to a predetermined maximum. The maximum is experimentally determined such that breakage of the rock will be visibly apparent throughout the axial extent of the column. [The breakage, of course, will not be visible until the material has been removed from the cylinder.] Thereafter, the remaining material is screened to remove the particles smaller than about 3350 microns, and an equivalent mass of fresh material from the granular supply is substituted therefor. The force application, screening and replenishment steps are repeated until the quantity of fresh material added each cycle stabilizes. "Stabilization" for the purpose of the exemplary protocol is deemed to have occurred when the amount of fines removed in a respective screening step is within 3% by mass of the amount of fines removed in the previous screening step and there is no increasing or decreasing trend in terms of the mass of the fines removed in the respective screening step and the two preceding screening steps.

For the purpose of this description and the accompanying claims, the final column which is compressed is defined as the test column, and each of the previous columns subjected to the compressive force is defined as a precursor column.

In addition to the crushing operation, the exemplary protocol also entails measurement and calculation operations.

Figure 1:
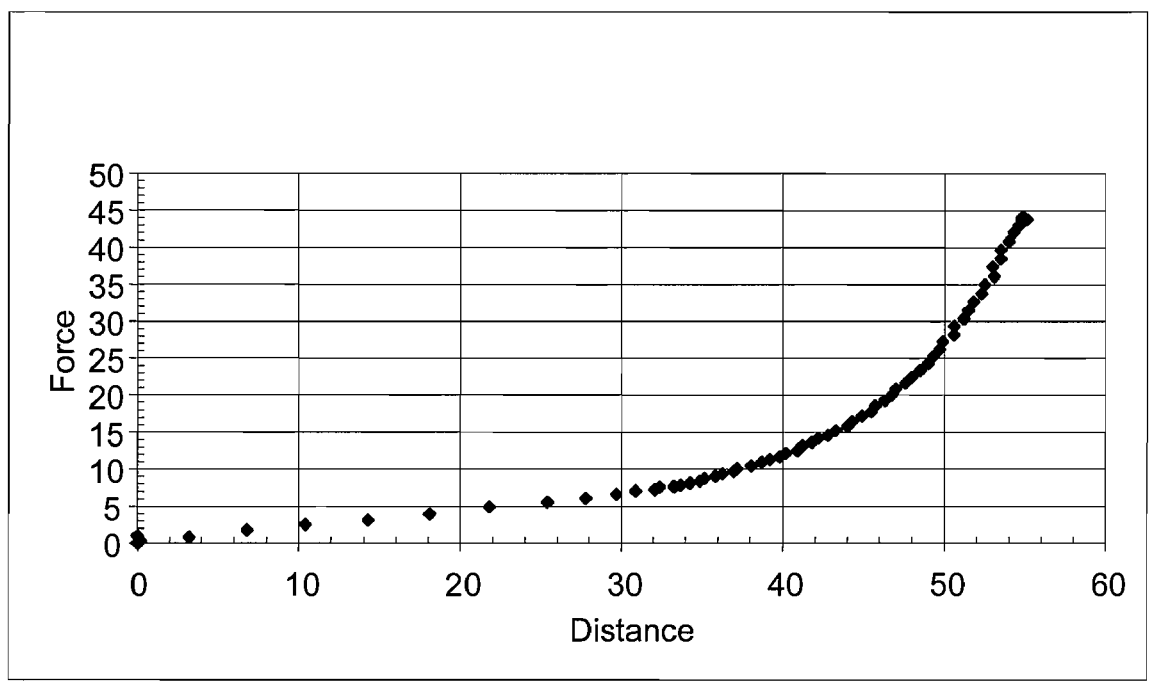
FIG. 1 is an exemplary plot of force v. distance data as obtainable by the protocol.

In the exemplary measurement operation, the amount by which the axial extent of each column is reduced through the application of the force is dynamically measured as the force is increased. FIG. 1 shows generally what a curve of force v. distance as obtainable in the protocol looks like; the exact shape of the curve varies, depending upon the rock used, etc.

In the exemplary calculation operation, the product of the force applied and the amount by which the axial extent of each column is reduced through the application of the force is calculated as an integral, and the rock is characterized on the basis of the average of the integrals calculated in respect of the test column and the two preceding precursor columns. For greater clarity, it will be understood that the integral associated with the hypothetical force-distance curve of FIG. 1 is represented by the area under the curve.

The foregoing provides a characteristic, $E_m$, of the rock. The actual value of $E_m$ obtained for any given rock will vary depending, inter alia, upon the size of the test column and sample mass utilized and will be expressed as a unit of mechanical energy.

For example, when force is measured in Newtons and distance is measured in meter, $E_m$ will be expressed in Joules.

Figure 2:
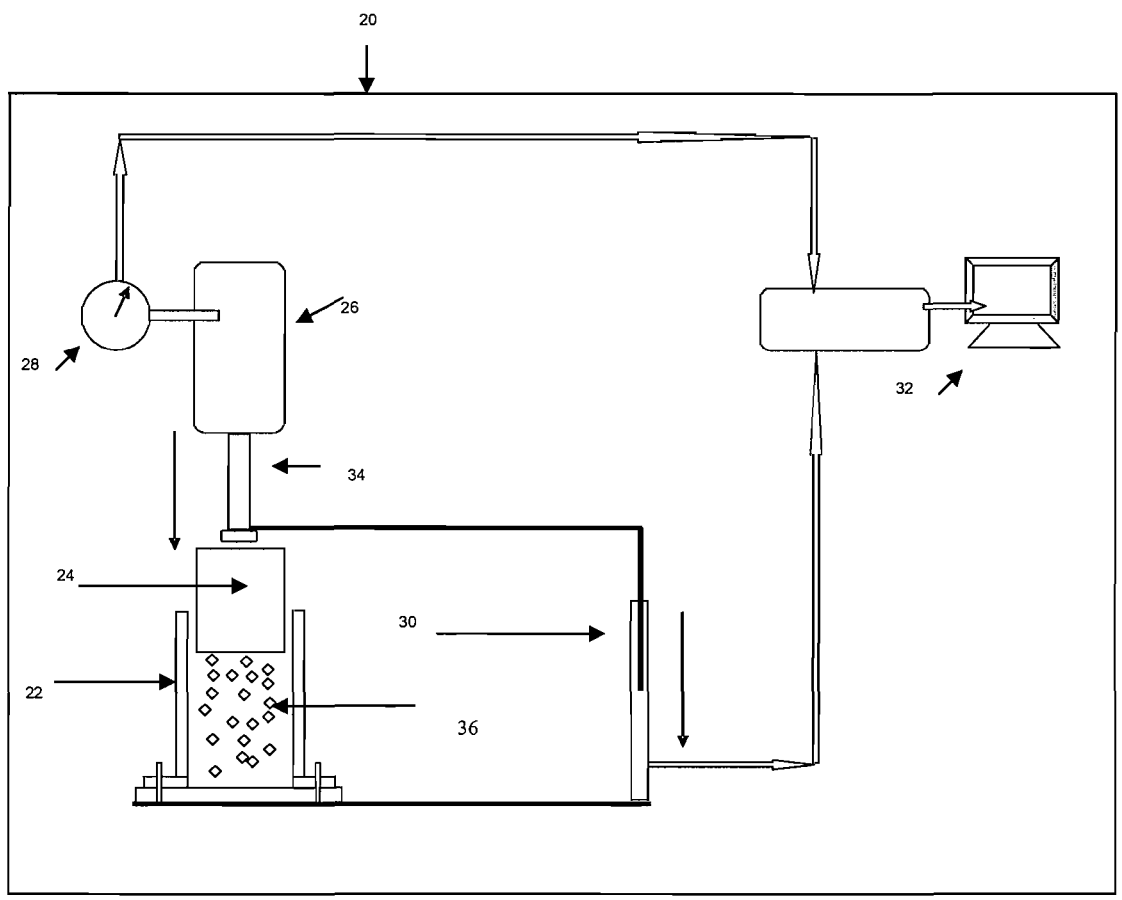
FIG. 2 is a sectional view of a cylinder, ram and data acquisition interface for use in the execution of the protocol according to an exemplary embodiment thereof.
Figure 3:
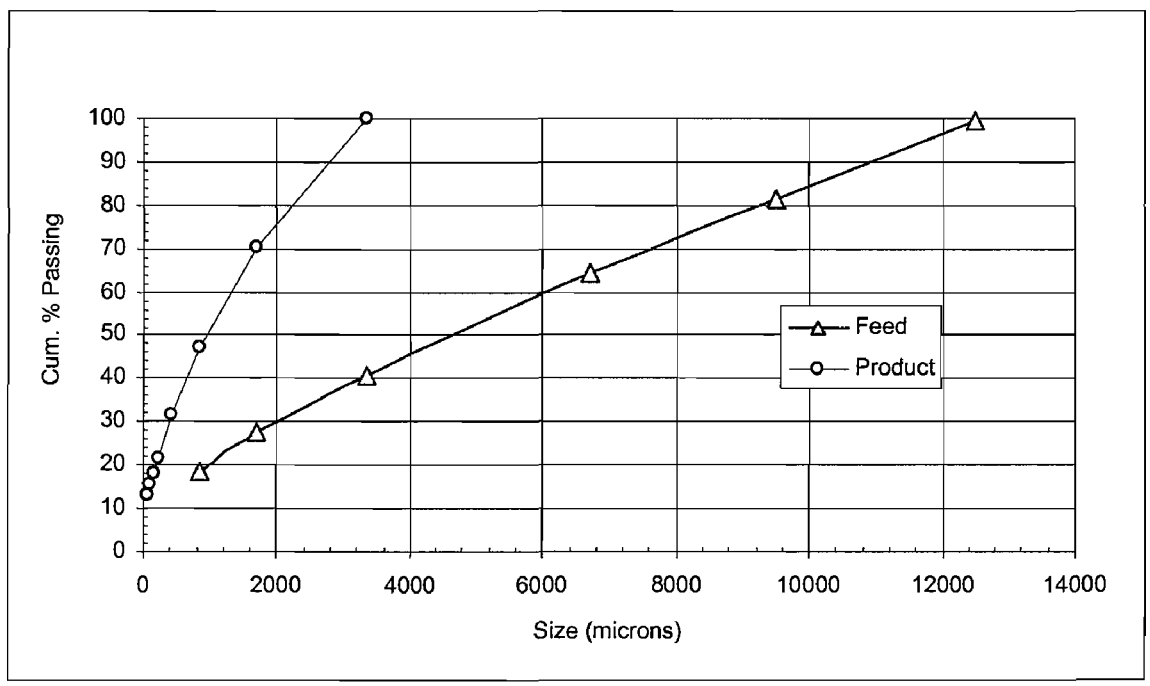
FIG. 3 is an exemplary plot of feed and product sizes as can be used in and obtainable by the protocol.

FIG. 2 shows an exemplary system 20 which may be conveniently used to carry out the protocol. The system 20 includes a vessel 22, a piston 24, a hydraulic press 26, a sensor 28, a potentiometer 30 and a computer and data acquisition interface 32.

The vessel 22 is a 100 mm ID cylindrical sample holder, sized to conveniently hold about 2 kg of granular rock and to maintain a uniform cross-section of the contents in columnar form 36. Piston 24 is adapted to reciprocate in close-fitting relation in sample holder 22 and to apply a compressive force to the contents thereof. The hydraulic press 26 has a ram 34 coupled to the piston 24 for generating the compressive force. The sensor 28 is for measuring hydraulic pressure in the press 26. The potentiometer 30 is attached to the ram 34 and the sample holder 22 and is calibrated to dynamically measure the precise distance moved, which is reflective of the change in the axial extent of the contents of the vessel, i.e. the respective rock column. The pressure sensor 28 measures the changing pressure inside the hydraulic press 26, the force applied to the column being a function of the hydraulic pressure and the area of the piston 24. The computer and data acquisition interface 32 is adapted to record the pressure inside the hydraulic press 26 and the distance moved simultaneously.

Persons of ordinary skill in the art will readily appreciate the manner in which such a system could be used to carry out the protocol. Accordingly, a detailed description is not necessary, nor provided herein.

However, for the benefit of those lacking ordinary skill in the art, it is noted that applying slight pressure to the contents of each column 36 prior to carrying out the crushing operation will serve to pack, but not crush, the granular material contained therein, so that the contents of the column can be quickly made to approximate the average bulk density of the granular supply (i.e. to avoid the need to allow time for the particulate materials therein to settle). Without intending to be bound by theory, minimizing the amount of packing energy included in the force-distance measurements is believed to improve accuracy.

For maximum reproducibility and correlation to real-world applications, it will normally be beneficial to control the maximum pressure of the ram such that, at the end of the crushing operation, the column 36 has characteristics similar to that of the material that might be expected to issue from a full-scale operation. For example, one would not apply unduly high pressure to diamond-bearing ore. To state it in another way, in the crushing operation, the force will normally be increased until the aggregate void volume of the compressed column is equivalent to the aggregate void volume of the output of the full-scale crushing device of interest.

The characteristic of the rock obtained by the protocol can be utilized advantageously in a number of ways.

For example, the protocol can be used to characterize the hardness of a subject rock. To do so, one would characterize, using the protocol, the rock as indicated above, making sure to measure the particle size of the feed material and the fines removed from each column.

The hardness of the rock can then be characterized using the formula $$HPI = \frac{E_m}{M \times (P_{80}^{-0.5} - F_{80}^{-0.5})}$$

where

HPI is the characterized rock hardness $E_m$ is the rock characteristic $F_{80}$ is the aperture size through which will pass 80% by mass of said equal amount by mass of the granular supply $P_{80}$ is the aperture size through which will pass 80% by mass of the fines removed from the test column after the crushing operation is performed thereon M is the mass of the amount of fines removed from the test column after the crushing operation was performed thereon The protocol can also be used as part of a method for calculating the amount of energy required to crush a rock from a given feed size to a given product size.

To do so, one would merely need to characterize the hardness as indicated previously, and then calculate the energy required using the formula $$E = HPI \times M \times (P_{80}^{-0.5} - F_{80}^{-0.5})$$

where

HPI is the characterized rock hardness

M is the mass of rock to be crushed

E is the energy required to crush the mass of rock $F_{80}$ is the feed size, defined as the aperture size through which will pass 80% by mass of the particles to be crushed $P_{80}$ is the product size, defined as the aperture size through which will pass 80% by mass of the particles after crushing As yet another use of the protocol, same can be used in a method for estimating the capacity of a crusher to crush a subject rock, said crusher having a known capacity for crushing a known rock. In this method, the hardness of the subject rock and the known rock are characterized as previously indicated, and the capacity of the crusher is estimated on the basis of the ratio of the hardnesses so determined.

To maximize accuracy in such calculation, in the crushing operations the compressive force is increased until the aggregate void volume of the respective compressed column is approximately equivalent to the aggregate void volume of the output of the crusher.

Whereas but a single protocol is herein described, various modifications can be made thereto.

For example, a two-cycle test can replace the longer version of the lock (i.e. steady state) cycle where the values of the complete lock cycle are graphed against the two cycle and the values for a complete test estimated.

As well, the size of the fines removed each cycle can be varied.

Additionally, the extent of breakage can be characterized on the basis of measurements other than $F_{80}$ and $P_{80}$. $F_{75}$ and $P_{75}$, for example, could be utilized with similar usefulness. Additionally breakage can be characterized on the basis of other exponents of $F_{80}$ and $P_{80}$ other than –0.5. Other exponents, –0.3, for example could be utilized with similar usefulness.

Of course, pistons and sample holders having different sizes and profiles other than circular could be readily utilized.

Yet other modifications are also contemplated. Indeed, it should be understood that the rock characteristic $E_m$ itself might be useful in certain circumstances, for example, in field tests where equipment associated with the measurement of particle sizes was not readily available.

In view of the foregoing, it should be understood that the present invention is to be limited only by the accompanying claims, purposively construed.

The invention claimed is:

1. A protocol for characterizing a rock, the protocol comprising:
a crushing operation, wherein a test column of said rock in granular form is subjected to a compressive force orientated parallel to the axis of said column;
a measurement operation, wherein the amount by which the axial length of the test column is reduced through the application of the force is measured; and
a calculation operation, wherein a characteristic of the rock is calculated using the product of the force applied and the amount by which the length of the test column is reduced through the application of the force.

2. A protocol according to claim 1, wherein: in the crushing operation, the force is increased over time; in the measurement operation, the distance by which the test column contracts as the force is increased is dynamically measured; and in the calculation operation, the product of the force applied and the amount by which the length of the test column is reduced is calculated as an integral.

3. A protocol according to claim 2, wherein in the crushing operation the force is increased at least until visible breakage of said rock is apparent throughout the axial extent of the test column.

4. A protocol according to claim 3, wherein in the crushing operation, the force is increased to a predetermined maximum.

5. A protocol according to claim 4, wherein:
   i. a granular supply of the rock is provided;
   ii. taken from the granular supply is a portion equal in mass to the test column;
   iii. the portion is formed into a precursor column;
   iv. the precursor column is subjected to a crushing operation to form a compressed column;
   v. the fines are removed from the compressed column;
   vi. the portion is replenished with an amount of the granular supply equal in mass to the fines removed; and
   vii. steps (iii)-(v) are repeated until the amount of the fines removed each time in step (v) has stabilized.

6. A protocol according to claim 5, wherein the final precursor column defines the test column.

7. A protocol according to claim 5, wherein the granular supply is obtained by crushing said rock to 100% passing through about 19000 micron mesh.

8. A protocol according to claim 5, wherein in step (v) the fines are removed from the compressed column by screening out the particles smaller than about 3350 microns therefrom.

9. A protocol according to claim 5, wherein the amount of fines removed is deemed to have stabilized when the amount of fines removed in a respective step (v) is within 3% by mass of the amount of fines removed in the previous step (v) and there is no increasing or decreasing trend in terms of the mass of the fines removed in the respective step (v), said previous step (v) and in the step (v) preceding said previous step (v).

10. A protocol according to claim 6, wherein
    in the crushing operation performed on each precursor column, the force is increased over time to said predetermined maximum;
    the amount by which the axial length of each precursor column is reduced in the crushing operation performed thereon is dynamically measured as the force is increased; and
    a product of the force applied to each precursor column and the amount by which the length of said each precursor column is reduced as the force is increased is calculated as an integral.

11. A protocol according to claim 10, wherein in the calculation operation, the characteristic of the rock is calculated as the arithmetic average of the integrals calculated in respect of the test column and the two precursor columns preceding the test column.

12. A method for characterizing the hardness of a subject rock,
    the method comprising the steps of:
      i. characterizing, using the protocol according to claim 5, said rock; and
      ii. characterizing the extent of the breakage experienced by the test column in the crushing operation performed thereon; and
      iii. characterizing the hardness as a function of the characteristic of the rock and the extent of the breakage.

13. A method according to claim 12, wherein the hardness of the rock is characterized according to the formula $$HPI = \frac{E_m}{M \times (P_{80}^{-0.5} - F_{80}^{-0.5})}$$

where
HPI is the characterized hardness of the rock
$E_m$ is the characteristic of the rock
$F_{80}$ is the aperture size through which will pass 80% by mass of said equal amount by mass of the granular supply
$P_{80}$ is the aperture size through which will pass 80% by mass of the fines removed from the test column after the crushing operation is performed thereon
M is the mass of the amount of fines removed from the test column after the crushing operation was performed thereon.

14. A method for calculating the amount of energy required to crush a rock from a feed size to a product size, said method comprising the steps of:
    i. characterizing the hardness of the rock using the method of claim 12;
    ii. calculating the amount of energy required to crush the rock using the formula $$E = HPI \times M \times (P_{80}^{-0.5} - F_{80}^{-0.5})$$

where
HPI is the characterized hardness of the rock
M is the mass of rock to be crushed
E is the energy required to crush the mass of rock
$F_{80}$ is the feed size, defined as the aperture size through which will pass 80% by mass of the particles to be crushed
$P_{80}$ is the product size, defined as the aperture size through which will pass 80% by mass of the particles after crushing.

15. A method for estimating the capacity of a crusher to crush a subject rock, said crusher having a known capacity for crushing a known rock, the method comprising the steps of:
    i. characterizing, using the method according to claim 12, the hardness of the subject rock and of the known rock; and
    ii. calculating the product of the known capacity and the ratio of the hardnesses characterized in (i) to arrive at the capacity of the crusher for crushing the subject rock.

16. A method according to claim 15, wherein in each crushing operation the force is increased until the aggregate void volume of the respective compressed column is equivalent to the aggregate void volume of the output of the crusher.

* * * * *